(12) United States Patent
Bressler et al.

(10) Patent No.: US 6,926,700 B2
(45) Date of Patent: Aug. 9, 2005

(54) NEEDLE ASSEMBLY

(75) Inventors: Peter W. Bressler, Philadelphia, PA (US); John Coleman, Philadelphia, PA (US); Mathieu Turpault, Berwyn, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/391,832

(22) Filed: Mar. 19, 2003

(65) Prior Publication Data

US 2003/0181867 A1 Sep. 25, 2003

Related U.S. Application Data

(60) Provisional application No. 60/365,479, filed on Mar. 19, 2002.

(51) Int. Cl.[7] ................................................ A61M 5/00
(52) U.S. Cl. ..................................................... 604/263
(58) Field of Search ............................... 604/192, 263, 604/110, 198, 187, 158

(56) References Cited

U.S. PATENT DOCUMENTS

| | | |
|---|---|---|
| 4,790,828 A | 12/1988 | Dombrowski et al. |
| 5,085,639 A | 2/1992 | Ryan |
| 5,088,982 A | 2/1992 | Ryan |
| 5,112,311 A | 5/1992 | Utterberg et al. |
| 5,120,320 A | 6/1992 | Fayngold |
| 5,154,699 A | 10/1992 | Ryan |
| 5,176,655 A | 1/1993 | McCormick et al. |
| 5,192,275 A | 3/1993 | Burns |
| 5,266,072 A | 11/1993 | Utterberg et al. |
| 5,290,264 A | 3/1994 | Utterberg |
| 5,423,766 A | 6/1995 | DiCesare |
| 5,562,636 A | 10/1996 | Utterberg |
| 5,562,637 A | 10/1996 | Utterberg |
| 5,735,827 A | 4/1998 | Adwers et al. |
| 5,951,525 A * | 9/1999 | Thorne et al. ............... 604/198 |

FOREIGN PATENT DOCUMENTS

JP          8-206195          8/1996

* cited by examiner

Primary Examiner—Kevin C. Sirmons

(57) ABSTRACT

The present invention is directed to a shieldable blood collection set and a needle assembly. The needle assembly includes a needle cannula having a puncture tip at a distal end, and a needle retraction mechanism including a hub portion at a proximal end which supports the needle cannula, a shield portion at a distal end, and an extendable member hingedly connected therebetween. The hub portion includes a lateral hub extension extending toward a distal end of the needle cannula, and the shield portion includes a lateral shield extension extending toward a proximal end of said needle cannula. Opposing lateral forces applied against the extendable member and an opposing lateral side of the needle retraction mechanism cause relative axial movement between the hub portion and the shield portion between a first sampling state with the puncture exposed, and a second shielded state with the puncture tip contained within the shield portion.

8 Claims, 8 Drawing Sheets

NEEDLE ASSEMBLY

CROSS REFERENCE TO RELATED APPLICATIONS

This application claims the benefit of U.S. Provisional Application No. 60/365,479 filed Mar. 19, 2002.

BACKGROUND OF THE INVENTION

1. Field of the Invention

The present invention relates to blood collection sets for safe and convenient handling of needles. More particularly, the present invention relates to a blood collection set including a needle assembly having a needle cannula which is retractable within a safety shield for protection from a used needle tip.

2. Description of Related Art

Disposable medical devices having medical needles are used for administering medication or withdrawing fluid from the body of a patient. Such disposable medical devices typically include blood collecting needles, fluid handling needles, and assemblies thereof. Current medical practice requires that fluid containers and needle assemblies used in such devices be inexpensive and readily disposable. Consequently, existing blood collection devices typically employ some form of durable, reusable holder on which detachable and disposable medical needles and fluid collection tubes may be mounted. A blood collection device of this nature may be assembled prior to use and then disassembled after use. Thus, these blood collection devices allow repeated use of a relatively expensive holder upon replacement of relatively inexpensive medical needles and/or fluid collection tubes. In addition to reducing the cost of collecting blood specimens, these blood collection devices help minimize the production of hazardous waste material.

A blood collection device or intravenous (IV) infusion device typically includes a needle cannula having a proximal end, a pointed distal end, and a lumen extending therebetween. The proximal end of the needle cannula is securely mounted in a plastic hub defining a central passage that communicates with the lumen extending through the needle cannula. A thin flexible thermoplastic tube is connected to the hub and communicates with the lumen of the needle cannula. The end of the plastic tube remote from the needle cannula may include a fixture for connecting the needle cannula to a blood collection tube or other receptacle. The specific construction of the fixture will depend upon the characteristics of the receptacle to which the fixture is to be connected.

In order to reduce the risk of incurring an accidental needle-stick wound, protection of used needle cannulas becomes important. With concern about infection and transmission of diseases, methods and devices to enclose or cover the used needle cannula have become very important and in great demand in the medical field. For example, needle assemblies commonly employ a safety shield that can be moved into shielding engagement with a used needle cannula to minimize risk of an accidental needle stick.

For example, U.S. Pat. No. 5,120,320 to Fayngold discloses an intravenous infusion set or a blood collection assembly with an automatic safety feature incorporating a needle cannula and a safety shield, in which the needle cannula can be pulled rearwardly such that the shield can be extended over the puncture tip of the needle. The assembly further includes flexible wings which can be used as means for securing the needle assembly to the skin of a patient during a medical procedure. Positioning of the shield over the needle, however, requires the user to maintain the shield with one hand while withdrawing the needle into the shield with the other hand, thus resulting in a complex two-handed operation for the medical practitioner.

U.S. Pat. No. 5,951,525 to Thorne et al. discloses a manually operated safety needle apparatus that includes two pairs of opposed legs adapted to move a shield of the apparatus to a position covering the used needle cannula. Such an assembly requires a complex arrangement with extensive mechanics for activation of the shield over the needle cannula, which can result in increased costs for manufacture and assembly. Additionally, activation of the needle assembly to move the shield into the proper position over the pointed distal end of the needle cannula requires movement of both pairs of legs toward each other, which can be awkward for the user.

In view of the foregoing, a need exists for a blood collection set including a shieldable needle assembly that achieves secure and effective shielding of a used needle cannula, which is simple and inexpensive to manufacture and easy to operate, and which has an improved ergonomic feel to the user.

SUMMARY OF THE INVENTION

The present invention is directed to a shieldable blood collection set, as well as a needle assembly for use in a blood collection set. The needle assembly includes a needle cannula having a proximal end and a distal end with a puncture tip, and a needle retraction mechanism having a hub portion at a proximal end thereof and a shield portion at a distal end thereof. The needle cannula is supported at its proximal end by the hub portion of the needle retraction mechanism, and extends through an internal passageway and out from an open end of the shield portion. The needle retraction mechanism includes opposing first and second lateral sides, with the hub portion including a lateral hub extension extending along the first lateral side in an axial direction toward the distal end of the needle cannula, and the shield portion including a lateral shield extension extending along the second lateral side in an axial direction toward the proximal end of the needle cannula.

The hub portion and the shield portion are adapted for relative axial movement with respect to each other between a first position in which the needle assembly is in a sampling state with the puncture tip of the needle cannula exposed from the open end of the shield portion, and a second position in which the needle assembly is in a shielded state with the puncture tip of the needle cannula contained within the shield portion. The needle retraction mechanism includes an extendable member hingedly connected between the hub portion and the shield portion at one of the first or second opposing lateral sides of the needle retraction mechanism for causing such relative axial movement. For example, the extendable member may include a pair of folding legs connected by a hinged knee joint, with one leg of the extendable member hingedly connected to the hub portion and the other leg of the extendable member hingedly connected to the shield portion. Opposing lateral forces applied against the extendable member and the opposing side of the needle retraction mechanism cause relative axial movement of the shield portion and the hub portion between the first position and the second position, thereby shielding the needle cannula.

The needle retraction mechanism may be in the form of a generally planar structure extending in a generally upright manner along the needle assembly, to form a generally fin-shaped structure for providing an ergonomic design for the user during insertion of the needle assembly into a patient. Desirably, the needle retraction mechanism includes a generally flat bottom surface.

The hub portion and the shield portion may include interengaging structure for permitting axial movement of the hub portion and the shield portion in opposing axial directions. For example, the shield portion may include a rail extending in an axial direction substantially parallel with the needle cannula, and the hub portion may include a guide channel for engagement with such a rail.

The needle assembly may further include structure for preventing relative axial movement of the hub portion and the shield portion from the second position to the first position after the assembly has been activated to the shielded state. For example, the extendable member may include a latch mechanism for engagement with the needle retraction mechanism when the hub portion and the shield portion are moved to the second position. Also, the shield portion may include a tip guard having a metallic spring clip mounted to the needle retraction mechanism, with the spring clip being biased against the needle cannula when the needle assembly is in the sampling state and being resiliently moved over the distal end of the needle cannula when the needle assembly is in the shielded state.

In a further embodiment, the present invention is directed to a needle assembly including a needle cannula having a proximal end and a distal end with a puncture tip, a hub member supporting the proximal end of the needle cannula, and a shield member including an internal passageway extending therethrough for accommodating the needle cannula. The hub member includes first and second lateral sides, as well as a lateral hub extension extending along the first lateral side in an axial direction toward the distal end of the needle cannula. The shield member also includes first and second lateral sides corresponding to the first and second lateral sides of the hub member, as well as a lateral shield extension extending along the second lateral side thereof in an axial direction toward the proximal end of the needle cannula. Also, the hub member further includes a hub leg hingedly extending from the lateral extension, while the shield member further includes a shield leg hingedly extending from the first lateral side thereof, with the hub leg and the shield leg hingedly connected to each other. The lateral hub extension and the lateral shield extension are engageable with each other to form a unitary structure, and the hub member and the shield member include interengaging structure for relative axial movement with respect to each other. Opposing lateral forces applied against the hinged connection between the hub leg and the shield leg and against the lateral shield extension cause relative axial movement of the shield member and the hub member between a first position in which the needle assembly is in a sampling state with the puncture tip of the needle cannula exposed from the shield member, and a second position in which the needle assembly is in a shielded state with the puncture tip of the needle cannula contained within the shield member, thereby retracting the needle and shielding the needle cannula.

In yet a further embodiment, the present invention is directed to a shieldable blood collection set including a fixture for connecting the blood collection set to a receptacle; a needle cannula having a proximal end and a distal end with a puncture tip; a flexible tube having a first end connected to the fixture and an opposed second end; a hub interconnecting the proximal end of the needle cannula and the second end of the flexible tube; and a shield including an internal passageway for accommodating the needle cannula. The hub and the shield include structure as defined in the needle assembly above, with the hub including a lateral hub extension extending laterally in an axial direction toward the distal end of the needle cannula and further including a hub leg hingedly extending from the lateral extension, and with the shield including a lateral shield extension extending laterally in an axial direction toward the proximal end of the needle cannula at a location opposing the lateral extension of the hub, and with the shield further including a shield leg hingedly extending therefrom, such that the hub leg and the shield leg are hingedly connected to each other. The lateral hub extension and the lateral shield extension are engageable with each other to form a unitary structure. Moreover, the hub and the shield include interengaging structure for relative axial movement with respect to each other between a first position in which the needle assembly is in the sampling state and a second position in which the needle assembly is in a shielded state. Opposing lateral forces applied against a hinged connection between the hub leg and the shield leg and against the lateral extension of the shield causes such relative axial movement, thereby retracting the needle and shielding the needle cannula.

DETAILED DESCRIPTION

Figure 1:
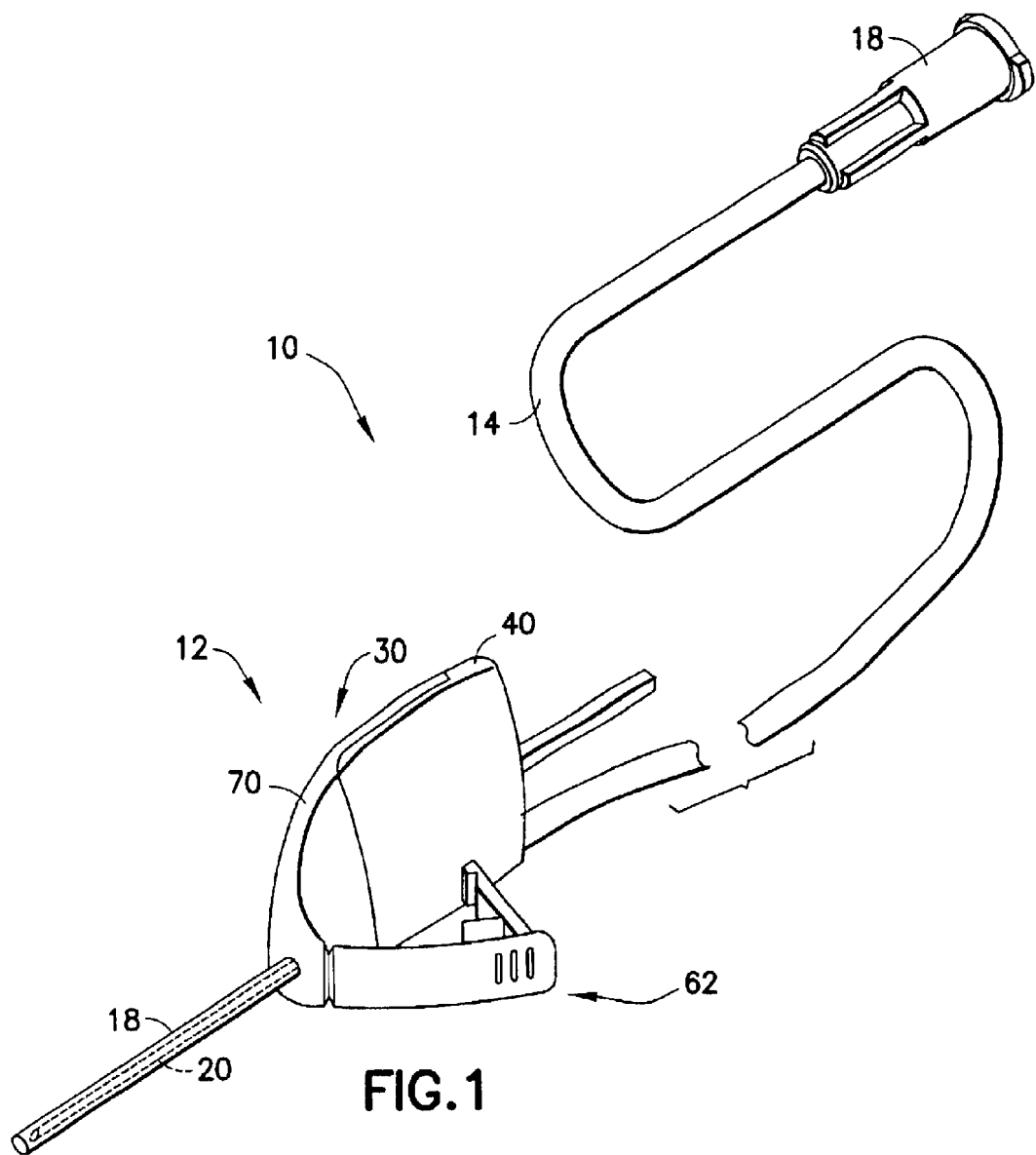
FIG. 1 is a perspective view of a blood collection set in accordance with the present invention.

Referring to the drawings in which like reference characters refer to like parts throughout the several views thereof, FIG. 1 illustrates a blood collection set 10 in accordance with the present invention and the related features. The present invention is generally described in terms of a blood collection set, and encompasses such a blood collection set as well as a shieldable needle assembly for use in such a blood collection set.

As shown in FIG. 1, blood collection set 10 includes a shieldable needle assembly 12, a flexible tube 14 extending from needle assembly 12 and a fixture 16 mounted to flexible tube 14. Shieldable needle assembly 12 of blood collection set 10 is shown in detail in FIGS. 2–7, and includes a needle cannula 20 and a needle retraction mechanism 30. Fixture 16 is connectable to a receptacle (not shown) for use in blood collection procedures, as is known in the art.

The shieldable needle assembly 12 of blood collection set 10 includes a needle cannula 20. Needle cannula 20 has a proximal end 22 and an opposing distal end 24. Needle cannula 20 defines a lumen 26 extending through needle cannula 20 from proximal end 22 to distal end 24. Distal end 24 of needle cannula 20 is beveled to define a sharp puncture tip 28, such as an IV puncture tip. Puncture tip 28 is provided for insertion into a patient's blood vessel, such as a vein, and is, therefore, designed to provide ease of insertion and minimal discomfort during venipuncture. A removable protective needle cover 18 may be positioned over distal end 24 of needle cannula 20 for protection from puncture tip 28 prior to use of blood collection set 10, as shown in FIG. 1.

The shieldable needle assembly 12 of the blood collection set 10 further includes a needle retraction mechanism 30. In general, needle retraction mechanism 30 includes proximal end 32, distal end 34, first lateral side 36, and second lateral side 38. Proximal end 32 of needle retraction mechanism 30 defines a hub portion or hub member 40, while distal end 34 of needle retraction mechanism 30 defines a shield portion or shield member 70. An extendable member 62 is interconnected between hub member 40 and shield member 70 at first lateral side 36. Hub member 40, shield member 70, and extendable member 62 are interengageable to form a unitary structure. As such, they may be formed as a single structure with hinged connections therebetween, for example through a molding process, and may be constructed of any known material, such as a thermoplastic material.

Figure 2:
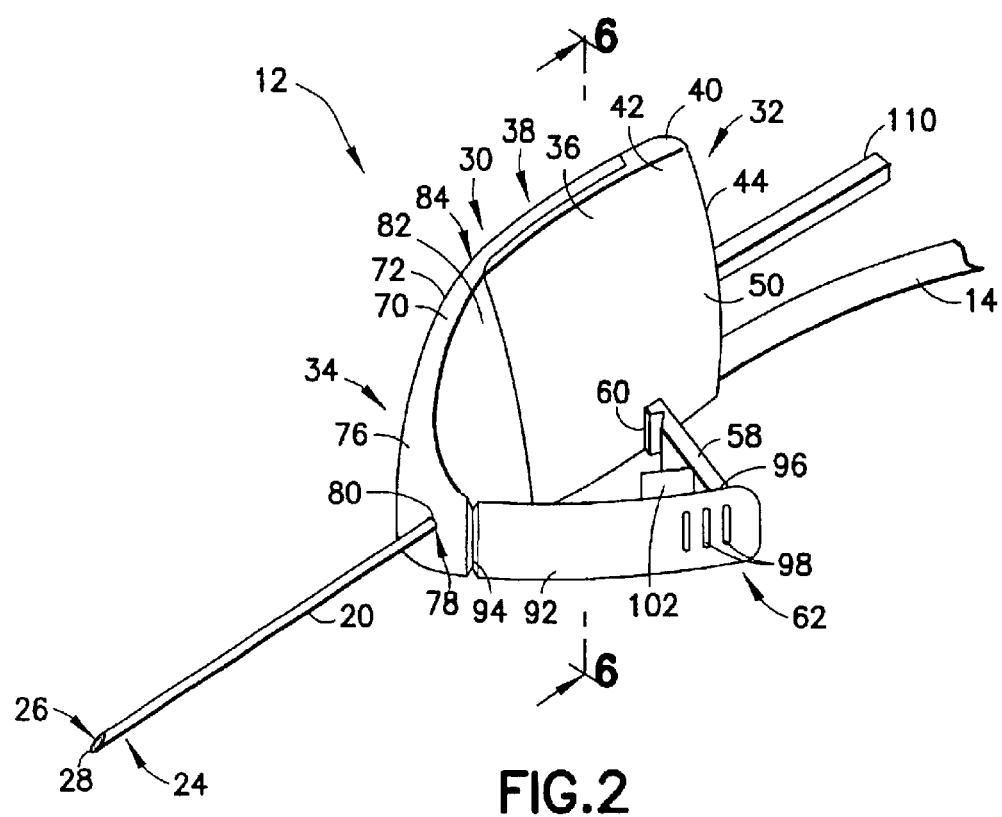
FIG. 2 is a perspective view of a needle assembly in accordance with the present invention shown in a sampling state.

As shown in FIGS. 1 and 2, with hub member 40 and shield member 70 interengaged to form a unitary structure, needle retraction mechanism 30 includes a generally planar structure which extends in a generally upright manner along needle assembly 12. Such an arrangement forms a generally fin-shaped structure, which provides an ergonomic feel for ease of use.

The hub member 40 of needle retraction mechanism 30 is generally defined by a housing 42, and includes proximal end 44 and distal end 46, with internal passage 48 extending from proximal end 44 to distal end 46. Hub member 40 further includes first lateral side 50 and second lateral side 52. Hub member 40 is adapted to support proximal end 22 of needle cannula 20. In particular, needle cannula 20 is positioned within internal passage 48 of hub member 40 and extends outward from distal end 46 of hub member 40. Preferably, needle cannula 20 and hub member 40 are formed as separate parts that are fixedly attached and secured through an appropriate medical grade adhesive, by direct mechanical attachment, or other similar means.

Hub member 40 further includes a lateral hub extension 54 extending along first lateral side 50 of hub member 40 to define distal end 46 of hub member 40. In particular, lateral hub extension 54 extends axially along first lateral side 36 of needle retraction mechanism 30 from hub member 40 in a direction toward distal end 34 of needle retraction mechanism 30 and distal end 24 of needle cannula 20, with hub member 40 further including hub shoulder 56 defined by the juncture of lateral hub extension 54 extending from hub member 40.

As described above, needle assembly 12 is provided for attachment to flexible tube 14, for example, for use in blood collection set 10. Hub member 40 may include a hub nub 64 for providing means for attachment of flexible tube 14 to needle assembly 12.

Needle retraction mechanism 30 of needle assembly 12 further includes shield member 70. The shield member 70 is generally defined by a housing 72, and includes proximal end 74 and distal end 76, with internal passage 78 extending from proximal end 76 to and through distal end 78 at distal opening 80. A portion of housing 72 defined by needle enclosure 90 extends co-axially about needle cannula 20, with internal passage 78 extending through needle enclosure 90 and in axial alignment with internal passage 48 of hub member 40.

Shield member 70 further includes first lateral side 82 and second lateral side 84. A lateral shield extension 86 extends along second lateral side 84 of shield member 70 to define proximal end 74 of shield member 70. In particular, lateral shield extension 86 extends axially along second lateral side 38 of needle retraction mechanism 30 from shield member 70 in a direction toward proximal end 32 of needle retraction mechanism 30 and proximal end 22 of needle cannula 20. Shield member 70 further includes shield shoulder 88 defined by the juncture of lateral shield extension 86 extending from shield member 70.

Lateral hub extension 54 and hub shoulder 56 of hub member 40 are interengageable with lateral shield extension 86 and shield shoulder 88 of shield member 70 to form a unitary structure for needle retraction mechanism 30. In particular, the leading edge of lateral hub extension 54, which forms distal end 46 of hub member 40, engages against the face of shield shoulder 88, while the leading edge of lateral shield extension 86, which forms proximal end 74 of shield member 70, engages against the face of hub shoulder 56. In this manner, lateral hub extension 54 and lateral shield extension 86 are adjacent each other at opposing lateral sides, thereby forming first lateral side 36 and second lateral side 38 of needle retraction mechanism 30. Such a unitary structure provides needle retraction mechanism 30 in a first position as shown in FIG. 2, in which needle assembly 12 is in a sampling state, with puncture tip 28 of needle cannula 20 extending through internal passage 78 and exposed from distal opening 80 of shield member 70.

Figure 3:
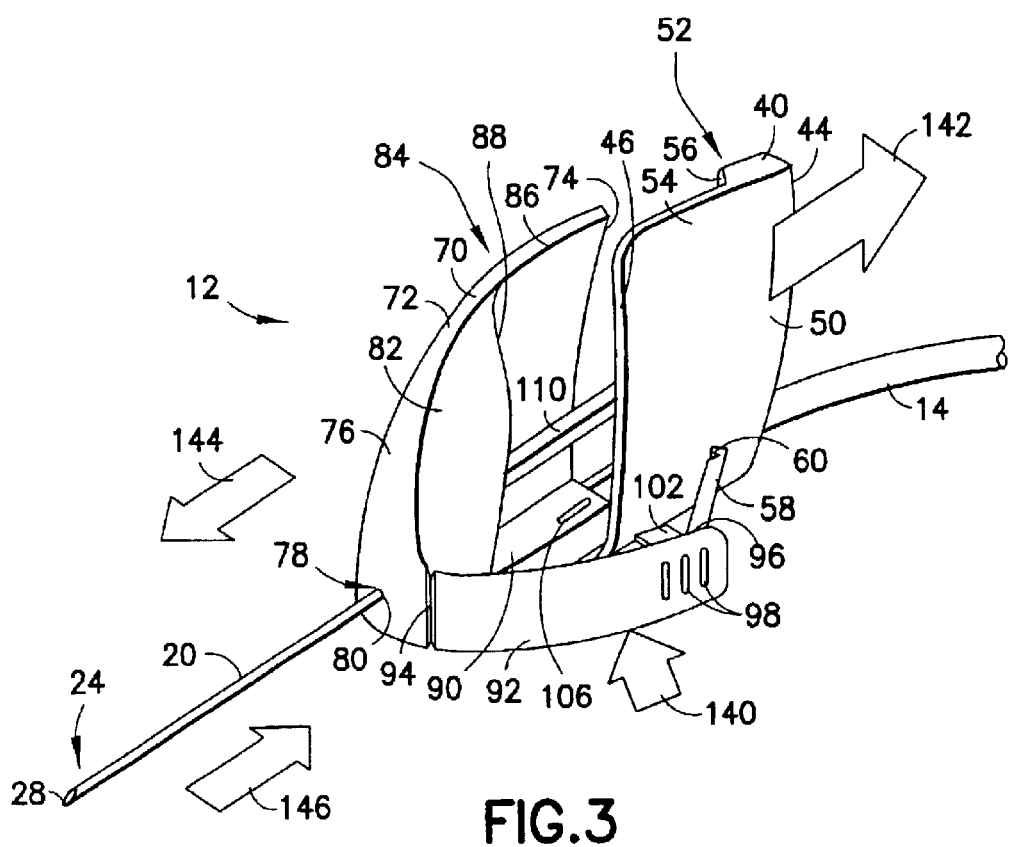
FIG. 3 is a perspective view of the needle assembly of FIG. 2 shown in a partially shielded state.
Figure 4:
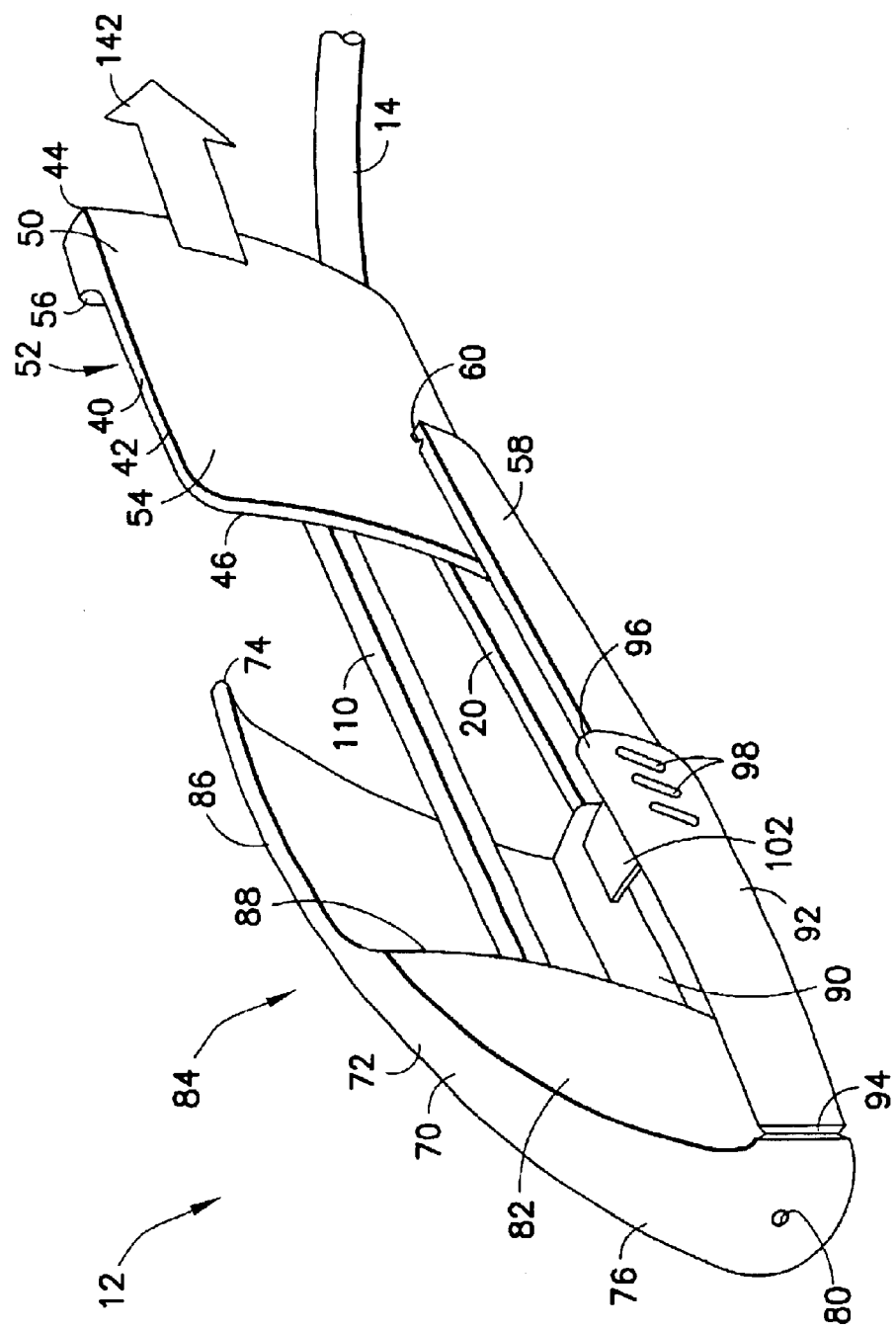
FIG. 4 is a perspective view of the needle assembly of FIG. 2 shown in a fully shielded state.

Shield member 70 and hub member 40 of needle retraction mechanism 30 are axially movable relative to each other in opposing axial directions, from this first position to a second position. In the second position, the shield member 70 and the hub member 40 are spaced from each other, with distal end 24 of needle cannula 20 contained within internal passage 78 of needle enclosure 90 of shield member 70, such that puncture tip 28 of needle cannula 20 does not extend beyond distal opening 80 of shield member 70 but is also contained within shield member 70. As such, when needle retraction mechanism 30 is in the first position, as shown in FIG. 2, the needle assembly 12 is in a sampling state, capable of venipuncture, as will be described in further detail. When needle retraction mechanism 30 is extended from the first position to the second position, as shown in FIGS. 3 and 4, needle cannula 20 is retracted within shield member 70 and the needle assembly 12 moves to a shielded state to protect the used puncture tip 28.

As noted, needle retraction mechanism 30 includes extendable member 62 extending from first lateral side 36 thereof. Hub member 40 includes hub leg 58 extending laterally from first lateral side 50 at lateral hub extension 54. Hub leg 58 is hingedly connected to lateral hub extension 54 through hinged connection 60. Moreover, shield member 70 includes shield leg 92 extending laterally from first lateral side 82. Shield leg 92 is hingedly connected to shield member 70 through hinged connection 94. Hub leg 58 and shield leg 92 extend toward each other at first lateral side 36 of needle retraction mechanism 30 to meet at hinged interconnection 96 forming a hinged knee joint. As such, the combination of hub leg 58 and shield leg 92 through the hinged connections 60 and 94, as well as hinged interconnection 96, form extendable member 62 of needle retraction mechanism 30. Extendable member 62 provides a mechanism for causing activation of needle retraction mechanism 30 through relative axial movement of hub member 40 and shield member 70 in opposing axial directions, as will be discussed in more detail herein.

Moreover, needle retraction mechanism 30 may include means for frictional engagement with a user's fingers in order to assist in activation to the shielded state. For example, shield leg 92 may include one or more protrusions such as shield leg ribs 98 on an outer surface thereof, and lateral shield extension 86 may similarly include a set of extension ribs 100 on second lateral side 84 of shield member 70. Such shield leg ribs 98 and extension ribs 100 provide means for frictional engagement with a user's fingers on opposing lateral sides of needle retraction mechanism 30.

Figure 5:
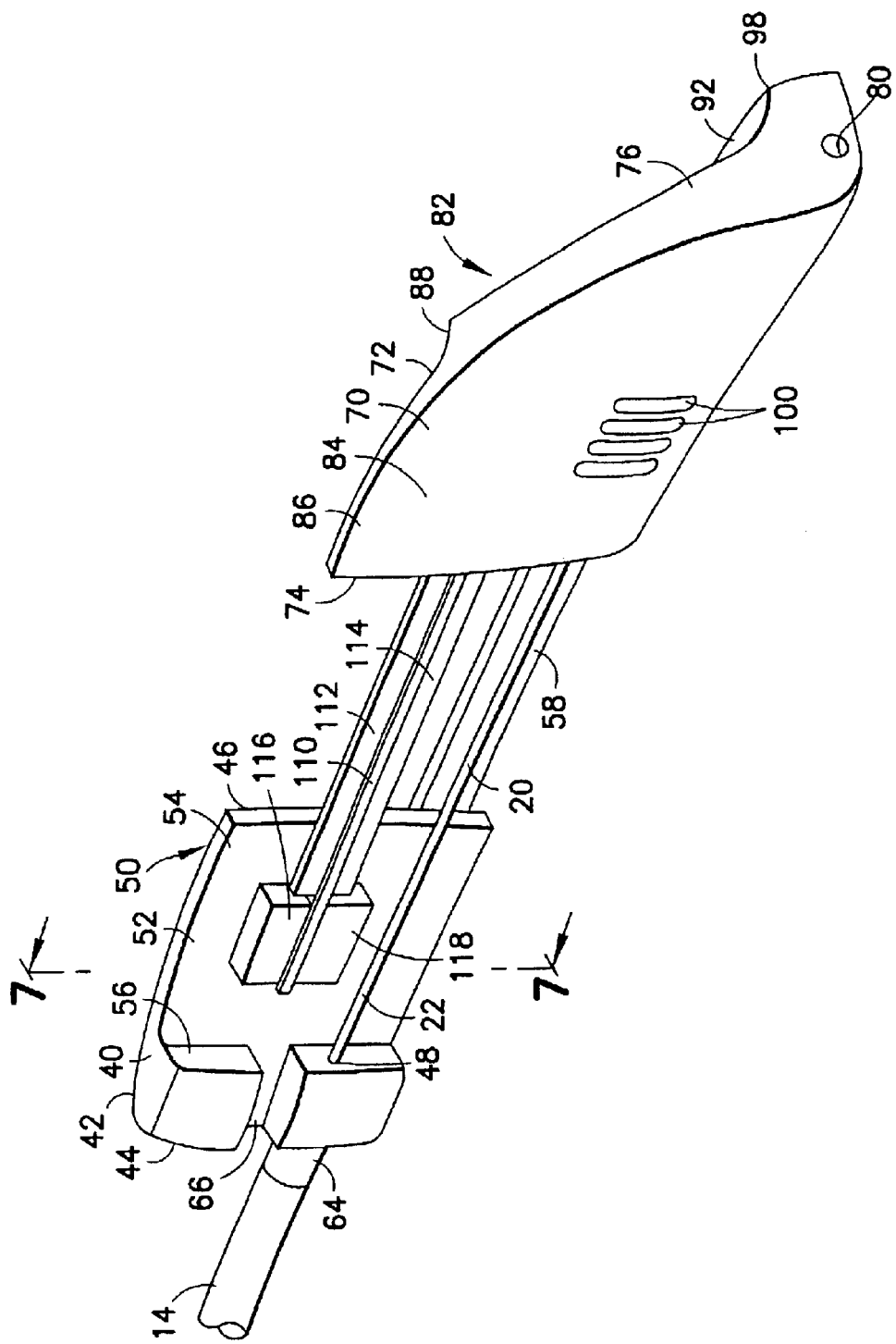
FIG. 5 is a reverse perspective view of the needle assembly of FIG. 4 shown in a fully shielded state.
Figure 6:
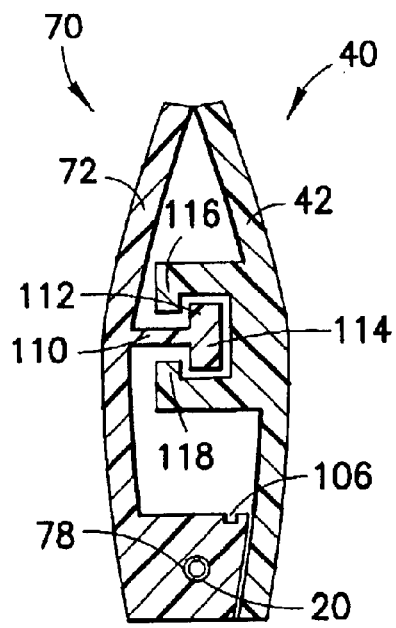
FIG. 6 is a cross-sectional view taken along line VI—VI of FIG. 2 with the needle assembly in a sampling state.
Figure 7:
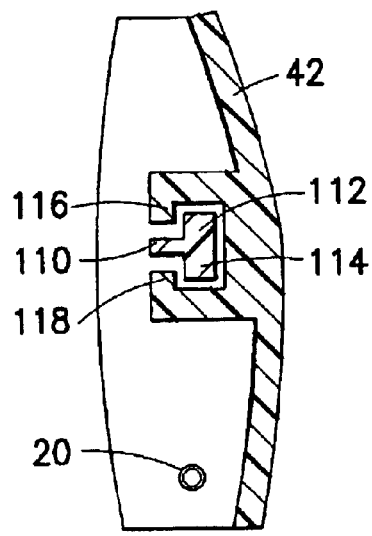
FIG. 7 is a cross-sectional view taken along line VII—VII of FIG. 5 with the needle assembly in a fully shielded state.

Hub portion 40 and shield portion 70 of needle retraction mechanism 30 may further include interengaging structure for permitting relative axial movement with respect to each other. For example, as seen in FIGS. 5–7, shield member 70 may include guide rail 110 extending from shield member 70 in a direction toward the distal end 34 of needle retraction mechanism 30. Such a guide rail 110 may extend from shield shoulder 88 and may be attached to the inner surface of lateral shield extension 86. Desirably, guide rail 110 may be integrally formed with shield member 70. Guide rail 110 may further include extension lips 112 and 114 extending in opposing directions from guide rail 110. Clasps 116 and 118 are provided on hub member 40 for engagement with extension lips 112 and 114. Clasps 116 and 118 may be integrally formed with hub member 40, and desirably extend from the inner surface of lateral hub extension 54 toward second lateral side 52 of hub member 40, establishing a hub channel 66 for accommodating guide rail 110. Clasps 116 and 118 are designed to interengage extension lips 112 and 114 of guide rail 110, to permit axial movement therealong, and to prevent disengagement therebetween. Also, guide rail 110 may include a stop means at the end thereof, for preventing clasps 116 and 118 from traveling axially beyond the end of guide rail 110 and becoming disengaged therefrom.

Additionally, needle retraction mechanism 30 may include means for preventing relative axial movement of hub member 40 and shield member 70 from the second position to the first position once needle assembly 12 has been activated from the sampling state to the shielded state, thereby preventing a re-exposure of needle cannula 20 and puncture tip 28. For example, as seen in FIGS. 2–4, extendable member 62 may include a latch mechanism extending from hub leg 58 or shield leg 92, such as a latch 102, for engagement with a portion of needle retraction mechanism 30 when hub member 40 and shield member 70 are moved axially away from each other to the second position when needle assembly 12 is moved into the fully shielded state. Latch 102 includes latch lip 104, which extends from latch 102. Latch lip 104 is provided for frictional engagement with opening 106, which extends through shield member 70, such as through the top portion of needle enclosure 90 of shield member 70. Extendable member 62 is designed such that, when needle retraction mechanism 30 is activated, hub leg 58 and shield leg 92 extend toward a co-linear position substantially parallel with needle cannula 20, thereby causing hub member 40 and shield member 70 to move in opposing axial directions. In such a co-linear position, latch 102 extending from shield leg 92 is moved to a position adjacent shield member 70, and latch lip 104 engages with opening 106. As such, extendable member 62 is locked in place, thereby locking needle assembly 12 in the shielded state.

Figure 8:
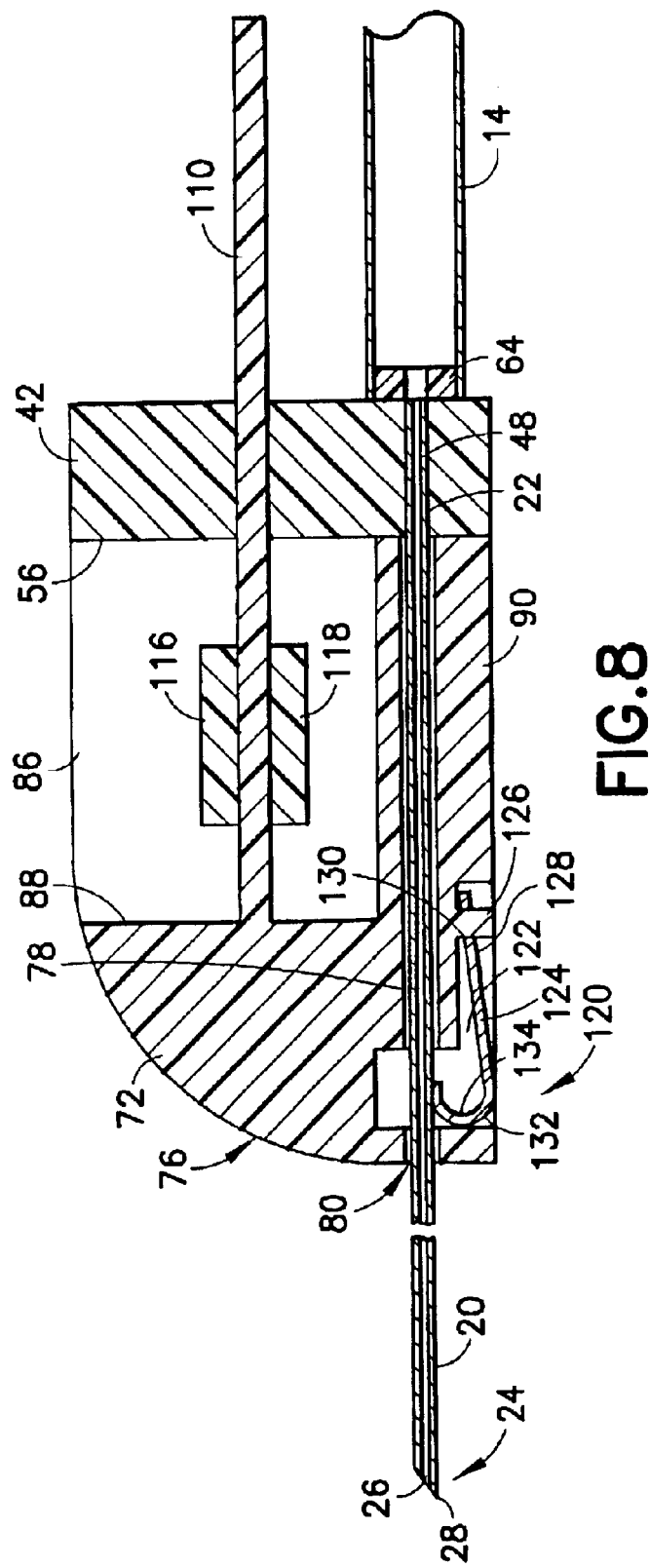
FIG. 8 is a side cross-section of a needle assembly in a sampling state in an alternate embodiment of the present invention including a tip guard assembly.
Figure 9:
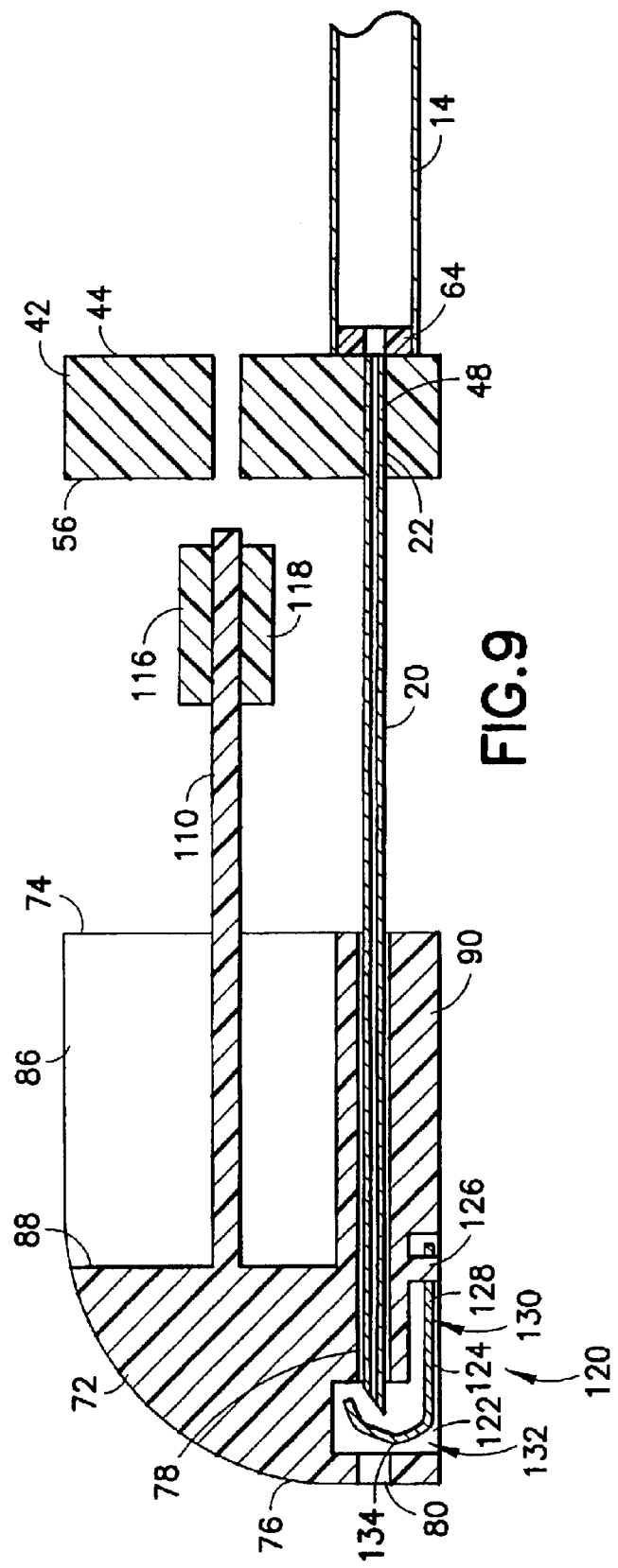
FIG. 9 is a side cross-section of a needle assembly in a shielded state in an alternate embodiment of the present invention including a tip guard assembly.

Alternatively or in addition to such a latch, needle assembly 12 may further include a tip guard, such as tip guard assembly 120, for providing a locking mechanism for preventing re-exposure of puncture tip 28 through distal opening 80 of shield member 70, as seen in FIGS. 8 and 9. Tip guard assembly 120 is desirably provided within a portion of shield member 70 adjacent distal end 76 thereof at internal clip receptacle 122. Tip guard assembly 120 includes a protective clip 124. A clip mounting post 126 extends downwardly from housing 72 of shield member 70, with clip 124 attached to housing 72 through clip mounting post 126. Clip 124 is unitarily stamped and formed from a resiliently deflectable metallic material. Clip 124 includes a planar spring leg 128 with a proximal end 130 and an opposed distal end 132. A lockout leg 134 extends angularly from distal end 132 of spring leg 128. Lockout leg 134 is bent back toward proximal end 130 of clip 124. The bends in lockout leg 134 enable secure protective engagement with puncture tip 28 of needle cannula 20 and further enable smooth axial sliding movement of tip guard assembly 120 along needle cannula 20, as described in further detail herein.

In an alternate embodiment, needle retraction mechanism 30 may further be provided with means for passively causing relative axial movement between hub member 40 and shield member 70 in opposing axial directions. For example, a compression spring (not shown) may be provided between hub member 40 and shield member 70, at a position such as at guide rail 110 or extending axially about needle cannula 20, between hub portion 40 and shield portion 70. Such a compression spring may be in a compressed state when needle retraction mechanism 30 is in the first position with hub member 40 and shield member 70 interfitting together. In such a compressed state, the compression spring stores energy for moving hub member 40 and shield member 70 axially apart. In such an embodiment, needle retraction mechanism 30 may include means for maintaining hub member 40 and shield member 70 in this interfitting engagement, thereby maintaining the compression spring in a compressed state. When released, the energy stored in the compression spring is released, thereby moving hub member 40 and shield member 70 in opposing axial directions, causing needle assembly 12 to be moved from the sampling state to the shielded state.

The overall profile and design of needle assembly 12 provides an ergonomic feel to the user. In particular, needle retraction mechanism 30 may include rounded lateral sides as best seen in FIGS. 6 and 7, and a flat bottom surface. Such a configuration provides for improved handling and operation during use.

With the basic structure of the blood collection set 10 and needle assembly 12 described, operation of the blood collection set 10 and needle assembly 12 will be described. In use, blood collection set 10 is provided with needle assembly 12 assembled as described and including flexible tube 14 extending from needle assembly 12 and connected to fixture 16. After removing blood collection set 10 from its package, it can be assembled with other appropriate medical equipment for use. For example, an appropriate receptacle, such as a non-patient needle assembly and a needle holder, may be connected to blood collection set 10 through fixture 16, thereby providing fluid communication with lumen 26 through needle cannula 20.

The needle assembly 12 is packaged in the sampling state, with needle cover 18 positioned over the distal end 24 of the needle cannula 20. To prepare for use of blood collection set 10, the user grasps blood collection set 10 at needle assembly 12 and removes the needle cover 18 to expose puncture tip 28 of needle cannula 20.

The medical practitioner then sterilizes the intended area of puncture on the patient's body, and can then urge puncture tip 28 at distal end 24 of needle cannula 20 into a targeted blood vessel of a patient. To insert the needle cannula 20, the user grasps needle assembly 12 on opposing first and second lateral sides 36 and 38 of needle retraction mechanism 30. The generally planar structure of needle retraction mechanism 30 extending in an upright manner forming a fin-shaped structure provides an ergonomic design for the user to assist in positioning the needle assembly 12 at the intended area of puncture on the patient's body. Once the puncture tip 28 of the needle cannula 20 is inserted into a blood vessel in the patient's body (i.e., venipuncture), the user may secure needle assembly 12 to the patient's body to maintain the positioning and placement of the needle assembly 12 during the medical procedure, for example, by taping retraction mechanism 62 in place with the flat bottom surface of needle retraction mechanism 30 lying flat against the patient's skin, or alternatively by rotating needle assembly 12, such that second lateral side 38 lies flat against the patient's skin and taping needle retraction mechanism 30 across first lateral side 36 of needle retraction mechanism.

After completing the appropriate medical procedure such as infusion or blood collection, the user of the blood collection set 10 and needle assembly 12 can activate needle assembly 12 to shield the puncture tip 28 with shield member 70. Activation can be accomplished while venipuncture is maintained, or after needle assembly 12 is removed from the patient. To activate needle assembly 12, the user grasps needle retraction member 30 between a finger and thumb at hinged interconnection 96 of extendable member 62 and at first lateral side 82 of shield member 70. Shield leg ribs 98 and extension ribs 100 provide a raised tactile surface for assisting the user in grasping of the needle retraction mechanism 30. The user then squeezes together against hinged interconnection 96 and first lateral side 82 in a direction toward the central axis of needle assembly 12 and toward needle cannula 20. Such squeezing forces extendable member 62 in a direction of arrow 140, through pivoting of hub leg 58 at hinged connection 60 and shield leg 92 at hinged connection 94, as well as pivoting of hub leg 58 and shield leg 92 with respect to each other at hinged interconnection 96. Such pivoting in turn forces hub member 40 and shield member 70 to move in opposing axial directions with respect to each other in a direction of arrows 142 and 144, respectively, from the first position as shown in FIG. 2, through the position of FIG. 3, and to the second position as shown in FIG. 4. The interengagement between clasps 116 and 118 of hub member 40 and guide rail 110 of shield member 70 permits such relative opposing axial movement of hub member 40 and shield member 70, and maintains the general upright orientation of hub member 40 and shield member 70 with respect to each other. Since proximal end 22 of needle cannula 20 is connected to hub member 40, such movement causes needle cannula 20 to axially move within internal passage 78 of shield member 70 in a direction of an arrow 146, and to retract within needle receptacle 90 of shield member 70. Continued squeezing force applied against extendable member 62 and second lateral side 84 causes distal end 24 and puncture tip 28 of needle cannula 20 to retract into distal opening 80 of shield member 70 and into needle receptacle 90, and causes shield leg 92 and hub leg 58 to extend to a generally co-linear position, thereby placing latch 102 at a position adjacent opening 106 of shield member 70. At such point, latch lip 104 can engage within opening 106, which provides a tactile feel to the user that hub member 40 and shield member 70 have moved to the second position, and effectively locks needle assembly 12 in the shielded position.

Moreover, in embodiments incorporating a tip guard assembly 120, clip 124 will automatically cover puncture tip 28 of needle cannula 20 once needle assembly 12 has been moved to the shielded state. In particular, as shown in FIGS. 8 and 9, when hub member 40 and shield member 70 are in the first position, needle cannula 20 extends outward from the housing 72 of the shield member 70 through distal opening 80. Opposing axial movement of hub member 40 and shield member 70 from the first position to the second position causes clip 124 to move along needle cannula 20 to the distal end 24. At this point, lockout leg 134 of clip 124 will pass distally beyond puncture tip 28 of needle cannula 20. The inherent resiliency of spring leg 128 of clip 124 will urge lockout leg 134 over puncture tip 28 of needle cannula 20. Thus, re-exposure of puncture tip 28 is prevented.

Furthermore, extendable member 62 has an overall dimension that will prevent movement of shield member 70 distally beyond needle cannula 20, and guide rail 110 may include stop means for preventing hub member 40 from moving beyond guide rail 110. Hence, puncture tip 28 of needle cannula 20 is safely shielded. Blood collection set 10 may then be appropriately discarded.

It is noted that while activation of the safety feature may require opposing squeezing forces applied against second lateral side 84 and against extendable member 62, as described above, needle retraction mechanism 30 may also including a passive activation feature, such as the compression spring described above. As such, passive shielding of needle assembly 12 can be achieved upon disengaging hub member 40 and shield member 70 from interfitting engagement, thereby providing needle assembly 12 as an automatically shieldable needle assembly.

While the needle assembly of the present invention has been described in terms of one embodiment for use in connection with a blood collection set, it is further contemplated that the needle assembly could be used with other medical procedures, such as in conjunction with a conventional IV infusion set, which are well known in the art for use with needle assemblies.

While the present invention is satisfied by embodiments in many different forms, there is shown in the Figures and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed is:

1. A needle assembly, comprising:
   a needle cannula having a proximal end and a distal end with a puncture tip;
   a hub member supporting the proximal end of the needle cannula, said hub member having first and second lateral sides and including a lateral hub extension extending along said first lateral side in an axial direction toward said distal end of said needle cannula, said hub member further including a hub leg hingedly extending from said lateral hub extension; and a shield member including an internal passageway extending therethrough for accommodating said needle cannula, said shield member having first and second lateral sides corresponding to said first and said second lateral sides of said hub member, said shield member including a lateral shield extension extending along said second lateral side thereof in an axial direction toward said proximal end of said needle cannula, said shield member further including a shield leg hingedly extending therefrom at said first lateral side with said hub leg and said shield leg hingedly connected to each other forming a single pair of hinged legs, wherein said shield member includes a rail extending in an axial direction substantially parallel with said needle cannula, and said hub member includes a guide channel for engagement with said rail, wherein said lateral hub extension and said lateral shield extension are engageable with each other to form a unitary structure; said hub member and said shield member include interengaging structures for relative axial movement with respect to each other between a first position in which said needle assembly is in a sampling state with said puncture tip of said needle cannula exposed from said shield member, and a second position in which said needle assembly is in a shielded state with said puncture tip of said needle cannula contained within said shield member; and wherein opposing lateral forces applied against said hinged connection between said hub leg and said shield leg and against said lateral shield extension cause said relative axial movement of said shield member and said hub member between said first position and said second position, thereby shielding said needle cannula.

2. A needle assembly as in claim 1, further comprising structure for preventing relative axial movement of said hub member and said shield member from said second position to said first position.

3. A needle assembly as in claim 2, wherein at least one of said hub leg or said shield leg includes a latch mechanism for engagement with at least one of said hub member or said shield member, respectively, when said hub member and said shield member are moved to said second position.

4. A shieldable blood collection set comprising:

a fixture for connecting the blood collection set to a receptacle;

a needle cannula having a proximal end and a distal end with a puncture tip;

a flexible tube having opposed first and second ends, said first end of said flexible tube being connected to said fixture;

a hub interconnecting said proximal end of said needle cannula and said second end of said flexible tube, said hub including a lateral hub extension extending laterally in an axial direction toward said distal end of said needle cannula, said hub further including a hub leg hingedly extending from said lateral extension; and a shield including an internal passageway for accommodating said needle cannula, said shield including a lateral shield extension extending laterally in an axial direction toward said proximal end of said needle cannula at a location opposing said lateral hub extension, said shield further including a shield leg hingedly extending therefrom with said hub leg and said shield leg hingedly connected to each other forming a single pair of hinged legs, wherein said shield includes a rail extending in an axial direction substantially parallel with said needle cannula toward said proximal end of said needle cannula, and said hub includes a guide channel for engagement with said rail, wherein said lateral hub extension and said lateral shield extension are engageable with each other to form a unitary structure; said hub and said shield include interengaging structure for relative axial movement with respect to each other between a first position in which said needle assembly is in a sampling state with said puncture tip of said needle cannula exposed from said shield, and a second position in which said needle assembly is in a shielded state with said puncture tip of said needle cannula contained within said shield; and wherein opposing lateral forces applied against said hinged connection between said hub leg and said shield leg and against said lateral shield extension causes said relative axial movement of said shield and said hub between said first position and said second position, thereby shielding said needle cannula.

5. A blood collection set as in claim 4, further comprising structure for preventing relative axial movement of said hub and said shield from said second position to said first position.

6. A blood collection set as in claim 5, wherein at least one of said hub leg or said shield leg includes a latch mechanism for engagement with at least one of said hub or said shield, respectively, when said hub and said shield are moved to said second position.

7. A blood collection set as in claim 4, further comprising a tip guard including a metallic spring clip mounted to said shield, said spring clip being biased against said needle cannula when said hub and said shield are in said sampling state and being resiliently moved over said distal end of said needle cannula when said hub and said shield are in said shielded state.

8. A blood collection set as in claim 4, further comprising a needle cover.

* * * * *